US006419976B1

(12) United States Patent
Ehlers et al.

(10) Patent No.: US 6,419,976 B1
(45) Date of Patent: *Jul. 16, 2002

(54) BEAN-NUT POPPING BEANS

(75) Inventors: Jeffrey D. Ehlers, Moreno Valley; Mark H. Sterner, Riverside, both of CA (US)

(73) Assignee: Inland Empire Foods, Inc., Riverside, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/405,279

(22) Filed: Sep. 23, 1999

Related U.S. Application Data

(63) Continuation-in-part of application No. 08/921,490, filed on Sep. 2, 1997, now Pat. No. 6,040,503.

(51) Int. Cl.[7] .................................................. A23L 1/20
(52) U.S. Cl. ........................ 426/634; 426/93; 426/629; 426/632
(58) Field of Search ................................ 426/634, 629, 426/632, 633, 93

(56) References Cited

U.S. PATENT DOCUMENTS

| 1,063,208 A | 6/1913 | Norton |
| 2,019,141 A | 10/1935 | Knowles |
| 2,278,467 A | 4/1942 | Musher |
| 2,278,475 A | 4/1942 | Musher |
| 2,278,941 A | 4/1942 | Musher |
| 2,282,783 A | 5/1942 | Musher |
| 3,617,309 A | 11/1971 | Rebane |
| 3,650,763 A | 3/1972 | Touba |
| 3,652,294 A | 3/1972 | Marotta et al. ................. 99/83 |
| 3,661,071 A | 5/1972 | Toei et al. |
| 3,738,848 A | 6/1973 | Mader |
| 3,754,930 A | 8/1973 | Toei et al. |
| 3,800,050 A | 3/1974 | Popel .......................... 426/343 |
| 4,006,260 A | 2/1977 | Webb et al. |
| 4,152,974 A | 5/1979 | Tienor ........................ 99/323.8 |
| 4,156,806 A | 5/1979 | Teich et al. |
| 4,409,250 A | 10/1983 | Van Hulle et al. ........... 426/242 |
| 4,450,180 A | 5/1984 | Watkins ....................... 426/107 |
| 4,548,826 A | 10/1985 | Watkins ....................... 426/394 |
| 4,585,660 A | 4/1986 | Sugisawa et al. |
| 4,691,374 A | 9/1987 | Watkins et al. .............. 383/104 |
| 4,724,290 A | 2/1988 | Campbell ............. 219/10.55 E |
| 4,737,376 A | 4/1988 | Brandlein et al. |
| 4,769,512 A | 9/1988 | Schulbach |
| 4,877,637 A | 10/1989 | Harp |
| 4,891,235 A | 1/1990 | Mizuguchi et al. |
| 4,990,348 A | 2/1991 | Spratt et al. ................. 426/242 |
| 5,044,777 A | 9/1991 | Watkins et al. .............. 383/100 |
| 5,183,678 A | 2/1993 | Taga et al. |
| 5,240,734 A | 8/1993 | Izzo et al. .................... 426/633 |
| 5,320,858 A | 6/1994 | Fazzolare et al. ........... 426/549 |
| 5,326,583 A | 7/1994 | Taga et al. |
| 5,366,754 A | 11/1994 | Rudan et al. ................ 426/633 |
| 5,409,729 A | 4/1995 | Friesen ........................ 426/625 |
| 5,421,253 A | 6/1995 | Reymeyer et al. ......... 99/323.5 |
| 5,436,023 A | 7/1995 | Avera et al. ................. 426/633 |
| 5,443,858 A | 8/1995 | Jensen et al. ............... 426/618 |
| 5,448,220 A | 9/1995 | Levy ........................... 340/539 |
| 5,478,986 A | 12/1995 | Westerburg ................. 219/411 |
| 5,518,755 A | 5/1996 | Wong et al. ................. 426/633 |
| 5,681,607 A | 10/1997 | Maki et al. .................. 426/595 |
| 5,688,543 A | 11/1997 | Freeport et al. .............. 426/93 |
| 5,694,830 A | 12/1997 | Hodgson et al. ........... 99/323.7 |
| 5,714,193 A | 2/1998 | Fix et al. ..................... 426/633 |
| 5,743,174 A | 4/1998 | Sickle .......................... 99/404 |
| 5,750,166 A | 5/1998 | Shellhaass .................... 426/93 |
| 5,753,287 A | 5/1998 | Chedid et al. ................ 426/93 |
| 5,770,839 A | 6/1998 | Ruebush et al. ............. 219/727 |
| 5,948,954 A | 9/1999 | Horn et al. .................. 800/264 |
| 5,996,480 A | 12/1999 | Kelley et al. |
| 6,040,503 A | 3/2000 | Ehlers et al. |

FOREIGN PATENT DOCUMENTS

| CH | 00147692 A | 5/1992 |
| JP | 56099765 A | 8/1981 |
| JP | 63148948 A | 6/1988 |

OTHER PUBLICATIONS

Enwere, N.J. et al., "Some chemical and physical properties of bambara groundnut (*Voandzeia subterranea* Thouars) seed and products," International Journal of Food Science and Nutrition 47:469–475(1996).

Uguru, M.I. et al., "Growth, Nodulation and Yield of Bambarra Groundnut (*Vigna subterranea* (L) Verdc) on Selected Nigerian Soils," *J. Sci Food Agric.* 73:377–382 (1997).

Database Abstract. Derwent–Acc–No: 1988–026623 for KR 8701616. Assignee: Agrin, Sep. 1987.*

Singh et al., "Patterns of variation in cultivated common bean (*Phaseolus vulgaris*, Fabaceae)," Economic Botany 43:39–57 (1989).

Tohmes et al., "Variability in Andean nuna common beans (*Phaseolus Vulgaris*, Fabaceae)," Economic Botany 49:78–95 (1995).

Van Beem et al., "Nutritive value of the nuna popping," Economic Botany 46:164–170 (1992).

"Lost crops on the Incas:," Little Known Plants of the Andes with Promise for Worldwide Cultivation, National Research Council Advisory Committee on Technology Innovation Board on science and Technology for Internation Development, 3–15 (1989).

(List continued on next page.)

Primary Examiner—Anthony J. Weier
(74) Attorney, Agent, or Firm—Brobeck Phleger & Harrison, LLP

(57) ABSTRACT

Novel snack foods, foodstuffs, and methods of producing the same from popping beans are claimed.

7 Claims, 3 Drawing Sheets

OTHER PUBLICATIONS

Spaeth et al., "Microstructure of Nunas: Andean Popping Beans," (*Phaseolus Vulgaris* L), Food Microstructure 8:263–269 (1989).

Zimmerer, Karl S., "Biological diversity and local development: 'Popping Beans' in the central andes," Mountain Research and Development 12(1):47–61 (1992).

Singh et al., Races of common bean (*Phaselous Vulgaris,* Fabaceae) Economic Botany 45(3):379–396 (1991).

Schenkel, Werner, "Bambar Groundnut in Indonesian," Sep. 29, 1999, pp. 1 and 2.

Heller, J., et al., "Bambara Groundnut," *Int. Plant Gen. Resources Institute,* 1997, pp. 6, 36–40.

Igbedioh, S., et al., "Effects of processing methods on Phytic acid level and some constituents in bambara groundnut (*Vigna subterranea*) and pigeon pea (*Cajanus cajan*)," *Food Chem.,* 50:147–151 (1994).

Goldringer, "Selection recurrente chez les autogames pour l'amelioration des varietes lignees pures," *Agronomie,* 13:561–577 (1993).

Kmiecik, et al., "Development of Nuna Beans with Temperate Zone Adaptation," *Annual Report of the Bean Improvement Cooperative,* 40:36–37 (1997).

* cited by examiner

BEAN-NUT POPPING BEANS

CROSS-REFERENCE TO RELATED APPLICATIONS

This application claims priority as a continuation-in-part application to Ehlers et al., BEAN-NUT POPPING BEANS, U.S. patent application Ser. No. 08/921,490, filed Sep. 2, 1997 now U.S. Pat. No. 6,040,503, herein incorporated by reference in its entirety including drawings.

FIELD OF THE INVENTION

This invention relates to foodstuffs and snack foods that derive from distinct bean varieties of *Phaseolus vulgaris* L that are capable of popping.

BACKGROUND OF THE INVENTION

The following is a discussion of the relevant art, none of which is admitted to be prior art to the appended claims.

Healthy, minimally processed snack foods such as dried fruits and roasted or toasted nuts and cereals can have a positive impact on the average person's diet and are an important and growing segment of the U.S. food industry. The development of toasted (not fried) snack foods from grain legumes are particularly desirable because these foods are naturally low in fat, and high in dietary fiber, protein, folic acid, and other nutrients.

"Nuñas" are a class of common beans found in the Andean region of South America. On heating, nuñas pop or expand, producing a toasted, soft-textured edible product. Nuñas are traditionally popped by rapidly heating them in a skillet with little or no oil (Zimmerer, 1992, *Mountain Research and Dev.* 12:47–61). Nuñas are presently cultivated in traditional farming systems as a climbing intercrop with maize (*Zea mays* L) by farmers in isolated pockets of Peru and Bolivia. Nuñas are adapted to cool, wet tropical highland areas, from 1,800 m to more than 2,800 m in elevation, and require 210 to 280 days to mature (Singh, 1989, *Econ. Botany* 43:39–57).

SUMMARY OF THE INVENTION

The present invention concerns a type of common bean (*Phaseolus vulgaris* L.) that rapidly expands (or "pops") upon heating, producing a toasted food which is softer in texture than a corn nut. In addition to being a tasty snack food item, "popping" beans could also have quality attributes useful to food processors, as for example, for energy-efficient preparation of "quick-cook" beans. The bean plants of the present invention possess early maturity, non-climbing growth habit, synchronous fruiting, photoperiod insensitivity and produce beans that possess the popping trait. In addition, the present invention concerns methods for producing such bean plants, and the popped bean product.

One advantage of the present invention is that the claimed popping bean varieties allow for high yields and economic production in the United States. The bean plants of the present invention can grow in the major bean growing regions in the United States including Idaho, North Dakota, Colorado, Michigan, Texas, California, and New York, i.e. any location where common beans (e.g., pinto, kidneys, small white, navy, etc.) are grown. Furthermore, the plants are capable of growth in any analogous climate worldwide.

The presently available accessions of nuñas will not produce grain under field conditions in the United States due to their late maturity (greater than 200 days) and extreme sensitivity to photoperiod. They do not flower when daylengths are about 12½ hours or longer. These factors cause the plant to flower too late to produce grain before the onset of cold weather in the Fall. Furthermore, the aggressive climbing growth habit and asynchronous fruiting makes them unsuitable for mechanized farming and once-over harvesting as is practiced in the United States.

In a first aspect, the invention features a bean plant of the species *Phaseolus vulgaris* which exhibits the phenotypic characteristics of early maturity, bush type growth habit, synchronous fruiting, photoperiod insensitivity, and which produces a popping bean.

Days to maturity are measured from planting to harvest. By "early maturity" it is meant that the plant reaches the dry pods stage in less than 200 days, and preferably in 90 days (+ or −5 days).

By "bush type growth habit" is meant compact in growth. Growth can either be determinant or indeterminant. In bush determinant growth the terminals of the plant end in reproductive organs (pods) and the plants generally attain a height of approximately 0.5 meters. In bush indeterminant growth the terminals remain vegetative and plants typically attain a height no greater than 0.75 meters. Bush type growth habit is in contrast to the characteristic aggressive climbing (twining) indeterminant growth displayed by nuñas, which are typically grown as intercrop with maize and often reach the top of the maize plant. Such plants often reach a height of 3 meters. Because these plants continue to grow, flowering and podding appear together. Nuñas begin fruiting at higher nodal positions on the mainstem and branches and there are more vegetative branches than plants that exhibit bush determinant or bush indeterminant growth. The plants of claimed invention do not exhibit flowers and dry pods together under normal growing conditions (i.e., when pod setting is normal).

By "synchronous fruiting" is meant that an individual plant produces a single flush of flowers of about two to three weeks duration followed by pod filling and uniform pod maturation. Concentrated flowering and fruiting periods allows for efficient "once-over" harvesting of the bean crop.

By "photoperiod insensitivity" is meant that the photoperiod response with respect to reproductive development of the plants is essentially eliminated. The plants are day neutral and can flower in day lengths longer than 13 hours.

By "popping bean" is meant a bean that changes texture and volume when subject to heat within a given range of moisture, time and pressure. A popped bean has a visible expansion in size and a detectable softening in texture compared with an unpopped bean. The conditions necessary to produce popping are known to those who practice the art. Beans can be popped by a variety of methods including: frying in oil, exposure to hot air, rotating on a hot sand bed, or rotary infrared. The beans produced by the plants of the present invention exhibit popping that is at least comparable to that exhibited by nuñas.

In preferred aspects: early maturity is a growing season of no greater than 100 days in which the plant reaches the dry pod stage; the photoperiod insensitivity is the ability to flower when daylengths are greater than or equal to 13 hours; and the bush type growth habit encompasses a height of less than 0.75 meter.

In a second aspect the invention features plant parts derived from a plant of claims 1–4 including leaves, stem, pollen, plant cells and seed.

In a third aspect, the invention cultivating the plant of claims 1–4.

In a fourth aspect, the invention features a seed produced from the plant of claims 1–4.

In a fifth aspect, the invention features a bean seed of the species *Phaseolus vulgaris* capable of germinating into a plant which exhibits early maturity, bush type growth habit, synchronous fruiting, photoperiod insensitivity, and which produces a popping bean.

In a sixth aspect, the invention features a bean seed produced by a cross of a nuña accession and a *Phaseolus vulgaris* cultivar exhibiting the characteristics of early maturity, bush type growth habit, synchronous fruiting, photoperiod insensitivity.

In preferred embodiments the nuña a accession is selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and W6 18720; the *Phaseolus vulgaris* cultivar is selected from the group consisting of small white, small red, navy, dark red kidney, light red kidney, black or black turtle, pink, pinto, cranberry, and canario.

In a seventh aspect the invention features a bean seed produced by a first cross of a first nuña accession and a *Phaseolus vulgaris* cultivar exhibiting the characteristics of early maturity, bush type growth habit, synchronous fruiting, and photoperiod insensitivity; a second cross of a second nuña accession and the *Phaseolus vulgaris* cultivar exhibiting the characteristics of early maturity, bush type growth habit, synchronous fruiting, photoperiod insensitivity; and a third cross of the offspring of the first and second crosses.

In preferred embodiments, the first and second nuña accessions are selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and W6 18720; the *Phaseolus vulgaris* cultivar is selected from the group consisting of small white, small red, navy, dark red kidney, light red kidney, black or black turtle, pink, pinto, cranberry, and canario.

In an eight aspect, the invention features a bean seed produced by a first cross of the Nuña accession No. PI316013 and a California Early Light Red Kidney line; a second cross of the Nuña accession No. PI316032 and a California Early Light Red Kidney line; and a third cross of the offspring of the first and second crosses.

In a ninth aspect, the invention features a bean suitable for popping produced from a species *Phaseolus vulgaris* which exhibits early maturity, bush type growth habit, synchronous fruiting, and photoperiod insensitivity.

In a tenth aspect, the invention features a popped bean from the species *Phaseolus vulgaris* that exhibits a texture less than that exhibited by a corn nut.

By "texture" is meant the shear force or compression or combination of the two required to deform the surface of a bean. The texture of a popped bean of the claimed invention is less than the texture exhibited by a corn nut, that is the shear force or compression or combination of the two is less than that required to deform the surface of a corn nut.

In a eleventh aspect, the invention features new and distinct plant varieties of *Phaseolus vulgaris* characterized by early maturity, bush type growth habit, synchronous fruiting, photoperiod insensitivity and which produce a popping bean.

In a twelfth aspect, the invention features a bean plant developed through hybridization characterized by genetic factors which confer early maturity, bush type growth habit, synchronous fruiting, photoperiod insensitivity, and production of a popping bean.

In a thirteenth aspect, the invention features a method of producing beans comprising self-pollinating a bean plant of the species *Phaseolus vulgaris* which exhibits the phenotypic characteristics of early maturity, bush type growth habit, synchronous fruiting, photoperiod insensitivity, and which produces a popping bean.

In a fourteenth aspect, the invention features a novel process to produce the beans of a bean plant which exhibits the phenotypic characteristics of early maturity, bush type growth habit, synchronous fruiting, photoperiod insensitivity, and which produces a popping bean comprising the steps of: (a) crossing plants grown from the beans of a nuña accession and a *Phaseolus vulgaris* cultivar exhibiting the characteristics of early maturity, bush type growth habit, synchronous fruiting, photoperiod insensitivity; (b) developing a pure plant line from the beans produced in (a), the plant line being selected for early maturity, bush type growth habit, synchronous fruiting, photoperiod insensitivity, and the ability to produce a popping bean; and (c) harvesting the beans of the pure plant variety which exhibits the phenotypic characteristics of early maturity, bush type growth habit, synchronous fruiting, photoperiod insensitivity, and which produces popping beans.

In preferred embodiments the nuña accession is selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and W6 18720; the *Phaseolus vulgaris* cultivar is selected from the group consisting of small white, small red, navy, dark red kidney, light red kidney, black or black turtle, pink, pinto, cranberry, and canario.

In a fifteenth aspect, the invention features a novel process to produce the beans of a bean plant which exhibits the phenotypic characteristics of early maturity, bush type growth habit, synchronous fruiting, photoperiod insensitivity, and which produces a popping bean comprising the steps of: (a) crossing plants grown from the beans of first nuña accession and a *Phaseolus vulgaris* cultivar exhibiting the characteristics of early maturity, bush type growth habit, synchronous fruiting, photoperiod insensitivity; (b) developing a pure plant line from the beans produced in (a), the plant line being selected for early maturity, bush type growth habit, synchronous fruiting, and the ability to produce popping beans; (c) crossing plants grown from the beans of a second nuña accession and the *Phaseolus vulgaris* cultivar exhibiting the characteristics of early maturity, bush type growth habit, synchronous fruiting, photoperiod insensitivity to develop $F_1$ plants; (d) crossing plants of the plant line of step (b) with said $F_1$ plants of step (c); (e) developing a pure plant line from the beans produced in (d), the plant line being selected for early maturity, bush type growth habit, synchronous fruiting, photoperiod insensitivity, and the ability to produce a popping bean; and (f) harvesting the beans of the pure plant variety which exhibits the phenotypic characteristics of early maturity, bush type growth habit, synchronous fruiting, photoperiod insensitivity, and which produces popping beans.

In preferred embodiments, the first and second nuña accessions are selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and W6 18720; the *Phaseolus vulgaris* cultivar is selected from the group consisting of small white, small red, navy, dark red kidney, light red kidney, black or black turtle, pink, pinto, cranberry, and canario.

In a sixteenth aspect, the invention features a novel process to produce the beans of a bean plant which exhibits the phenotypic characteristics of early maturity, bush type growth habit, synchronous fruiting, photoperiod insensitivity, and which produces a popping bean comprising the steps of: (a) crossing plants grown from the beans of the Nuña accession No. PI316013 and California Early Light Red Kidney;(b) developing a pure plant line from the beans produced in (a), the plant line being selected for early maturity, bush type growth habit, synchronous fruiting, and the ability to produce popping beans; (c) crossing plants grown from the beans of the Nuña accession No. PI316032 and California Early Light Red Kidney to develop $F_1$ plants; (d) crossing plants of the plant line of step (b) with the $F_1$ plants of step (c); (e) developing a pure plant line from the beans produced in (d), the plant line being selected for early maturity, bush type growth habit, synchronous fruiting, photoperiod insensitivity, and the ability to produce a popping bean; and (f) harvesting the beans of the pure plant variety which exhibits the phenotypic characteristics of early maturity, bush type growth habit, synchronous fruiting, photoperiod insensitivity, and which produces popping beans.

In a seventeenth aspect, the invention features seed produced by (a) crossing plants grown from the beans of a nuña accession and a *Phaseolus vulgaris* cultivar exhibiting the characteristics of early maturity, bush type growth habit, synchronous fruiting, photoperiod insensitivity; (b) developing a pure plant line from the beans produced in (a), the plant line being selected for early maturity, bush type growth habit, synchronous fruiting, photoperiod insensitivity, and the ability to produce a popping bean; and (c) harvesting the beans of the pure plant variety which exhibits the phenotypic characteristics of early maturity, bush type growth habit, synchronous fruiting, photoperiod insensitivity, and which produces popping beans.

In preferred embodiments the nuña accession is selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and W6 18720; the *Phaseolus vulgaris* cultivar is selected from the group consisting of small white, small red, navy, dark red kidney, light red kidney, black or black turtle, pink, pinto, cranberry, and canario.

In an eighteenth aspect, the invention features beans produced by (a) crossing plants grown from the beans of first nuña accession and a *Phaseolus vulgaris* cultivar exhibiting the characteristics of early maturity, bush type growth habit, synchronous fruiting, photoperiod insensitivity; (b) developing a pure plant line from the beans produced in (a), the plant line being selected for early maturity, bush type growth habit, synchronous fruiting, and the ability to produce popping beans; (c) crossing plants grown from the beans of a second nuña accession and the *Phaseolus vulgaris* cultivar exhibiting the characteristics of early maturity, bush type growth habit, synchronous fruiting, photoperiod insensitivity to develop $F_1$ plants; (d) crossing plants of the plant line of step (b) with the $F_1$ plants of step (c); (e) developing a pure plant line from the beans produced in (d), the plant line being selected for early maturity, bush type growth habit, synchronous fruiting, photoperiod insensitivity, and the ability to produce a popping bean; and (f) harvesting the beans of the pure plant variety which exhibits the phenotypic characteristics of early maturity, bush type growth habit, synchronous fruiting, photoperiod insensitivity, and which produces popping beans.

In preferred embodiments, the first and second nuña accessions are selected from the group consisting of accession numbers W6 4296, W6 4297, W6 4298, PI 298820, PI 298822, PI 298824, PI 316013, PI 316014, PI 316016, PI 316017, PI 316018, PI 316019, PI 316020, PI 316021, PI 316022, PI 316023, PI 316024, PI 316025, PI 316029, PI 316030, PI 316031, PI 316032, PI 390771, PI 390775, PI 511763, PI 511767, PI 531862, PI 577677, PI 577678, PI 577679, PI 577680, PI 577682, and W6 18720; the *Phaseolus vulgaris* cultivar is selected from the group consisting of small white, small red, navy, dark red kidney, light red kidney, black or black turtle, pink, pinto, cranberry, and canario.

In a nineteenth aspect, the invention features beans produced by (a) crossing plants grown from the beans of the Nuña accession No. PI316013 and California Early Light Red Kidney; (b) developing a pure plant line from the beans produced in (a), the plant line being selected for early maturity, bush type growth habit, synchronous fruiting, and the ability to produce popping beans; (c) crossing plants grown from the beans of the Nuña accession No. PI316032 and California Early Light Red Kidney to develop $F_1$ plants; (d) crossing plants of the plant line of step (b) with plants of step (c); (e) developing a pure plant line from the beans produced in (d), the plant line being selected for early maturity, bush type growth habit, synchronous fruiting, photoperiod insensitivity, and the ability to produce a popping bean; and (f) harvesting the beans of the pure plant variety which exhibits the phenotypic characteristics of early maturity, bush type growth habit, synchronous fruiting, photoperiod insensitivity, and which produces popping beans.

In a twentieth aspect, the invention features progeny plants produced from the beans of claims 8, 9, 10, 11, 12, 13, 14, 15, 28, 29, or 30.

In a twenty-first aspect, the invention features a plant cell derived from the plant or a progeny plant of claims 1, 18, 19, or 31.

The present invention also contemplates progeny plants or plant cells produced from the seed or plants of the present invention. The progeny plants or progeny plant cells may be produced using art recognized in vivo, in vitro and breeding methods. Progeny as used herein refers to any descendant, including a descendant removed by many generations from a particular related plant.

The present invention also contemplates variants, mutants and modifications of the claimed bean plants including improvements such as a higher percentage of popping of beans, greater yield, improved favor, improved texture and pest resistance. Such improvements are possible by using standard plant breeding procedures.

In a twenty-second aspect, the invention features a foodstuff or snack food derived from any of the previously discussed aspects and embodiments. In one preferred embodiment, the foodstuff or snack food is a homogenized, blended peanut butter-like spread. In other preferred embodiments, the snack food is simply the popped nut, with or without added flavoring. This product is capable of being packaged and dispensed conveniently in vending machines. In still further embodiments, the snack food is dispensed into jars or other containers, or in microwaveable bags having instructions for convenient home or workplace popping. Flavoring components may be also be incorporated along with the unpopped beans and effectively incorporated on and about the popped beans before, during, and/or after popping.

Popping is accomplished using rapid heating means such as hot air, oil, microwave, infrared, superheated steam, or hot particulate matter such as salt or sand. These rapid heating means can effectively "pop" the raw beans to achieve a palatable texture and taste uncharacteristic of the starting product. Applicants have succeeded in converting otherwise unamenable cultivars into popping cultivars via a seed-conditioning step preceding the rapid application of heat.

In terms of the conditioning step, the Applicants have noted that starting seed moisture content appears critical to the success of the popping phenomenon but can vary according to the exact heating method employed and possibly also to exact cultivar identity and conditioning, if any. Beans having an upper threshold moisture content of about 15% and greater do not substantially pop, whereas beans having lower moisture contents, preferably 7–12%, more preferably about 7–9% pop well. However, rapid heating means employing oil exact a somewhat lesser requirement, i.e. permit a higher starting moisture content that still allows for good popping.

There are primarily two components of the instant invention that make it work: selection or conditioning of Product grains to have a suitable grain moisture content at the time of "popping," and the rapid application of sufficient heat for sufficient time to induce popping. These parameters will vary depending on, for example, the precise product cultivar used, the atmospheric conditions in which the beans are grown or exposed, the conditioning method employed, if any, and the specific means of heating employed. Suitable variance of these parameters, however, is well within the skilled artisan's knowledge and abilities.

Optimum and preferred aspects of the invention include products generated from and processes entailing the popping of raw or preconditioned beans having a suitable or conditionable moisture content of preferably between about 5–15% (w-w), more preferably about 7–12%, most preferably about 7–9%, and which yields the desired product when exposed to rapid and suitable heat or energy transfer. Use of oil heating allows the moisture content to be greater, up to about 14+%. Hot air, oil, particulate matter and superheated steam popping are all generally achieved using temperatures between about 110 and 260° C, for approximately 1–10 minutes, depending on the specific method used. Hot air of about 140–180° C. takes about 1–2 minutes, and most usually between about 50 seconds and 1.5 minutes. Oil frying generally requires less time (~30–60 seconds) and microwave cooking may require ~2–4 minutes, depending on the exact microwave unit used. Particulate matter cooking, depending on how fine the particulate matter is and temperature, may approximate oil in terms of time necessary to pop and likely is intermediate between hot air and oil. Coarser matter is likely to take longer than fine matter at the same temperature. The skilled artisan knows that cooking time can vary to accommodate the factors mentioned. Routine experimentation may be employed to conveniently map optimal parameters.

DETAILED DESCRIPTION

All references and patents cited herein are hereby incorporated by reference in their entireties, word-for-word, drawing-for-drawing, and are not intended to be admitted prior art. Moreover, the examples and discussion herein are merely illustrative of the nature of the invention and not intended to be limiting as to true scope and spirit.

DETAILED DESCRIPTION

I. Breeding

The following Example is provided for further illustrating various plant breeding aspects and embodiments of the present invention and is in no way intended to be limiting in scope.

EXAMPLE 1

Production of a *Phaseolus vulgaris* Plant "Popping Bean"Species which Exhibits Early Maturity, Bush type Growth Habit, Synchronous Fruiting and Photoperiod Insensitivity The methods utilized to produce the bean plants of the present invention are traditional plant breeding procedures and the pedigree method of plant breeding, all of which are familiar to those who practice the art.

Pedigree breeding and recurrent selection breeding methods are used to develop inbred lines from breeding populations. Breeding programs combine desirable traits from two or more inbred lines or various broad based sources into breeding pools from which new inbred lines are developed by selfing and the selection of desired phenotypes.

Pedigree breeding starts with the crossing of two genotypes, each of which may have one or more desirable characteristics that is lacking in the other or which complement the other. In pedigree breeding method, the superior plants of the segregating generations are identified, selfed and selected in successive generations. In the succeeding generations the heterozygous condition gives way to homogeneous lines as the result of self-pollination and selection. Typically in the pedigree method of plant breeding five or more generations of selfing and single plant selection is practiced.

Figure 1:
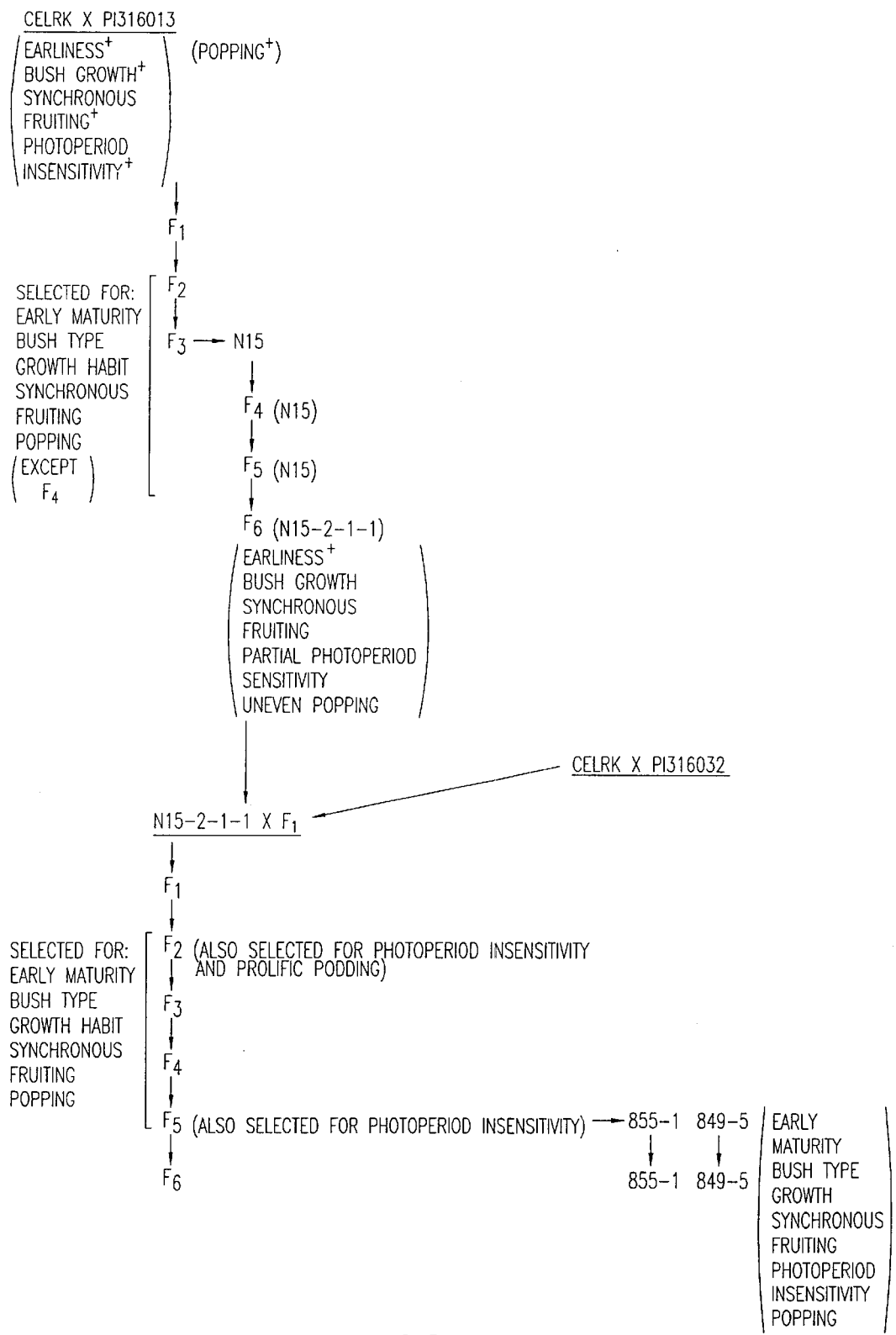
FIG. 1 is a representation of the crosses and selfs carried out to produce a *Phaseolus vulgaris* plant "popping bean" species that exhibits early maturity, bush type growth habit, synchronous fruiting and photoperiod insensitivity.
Figure 2:
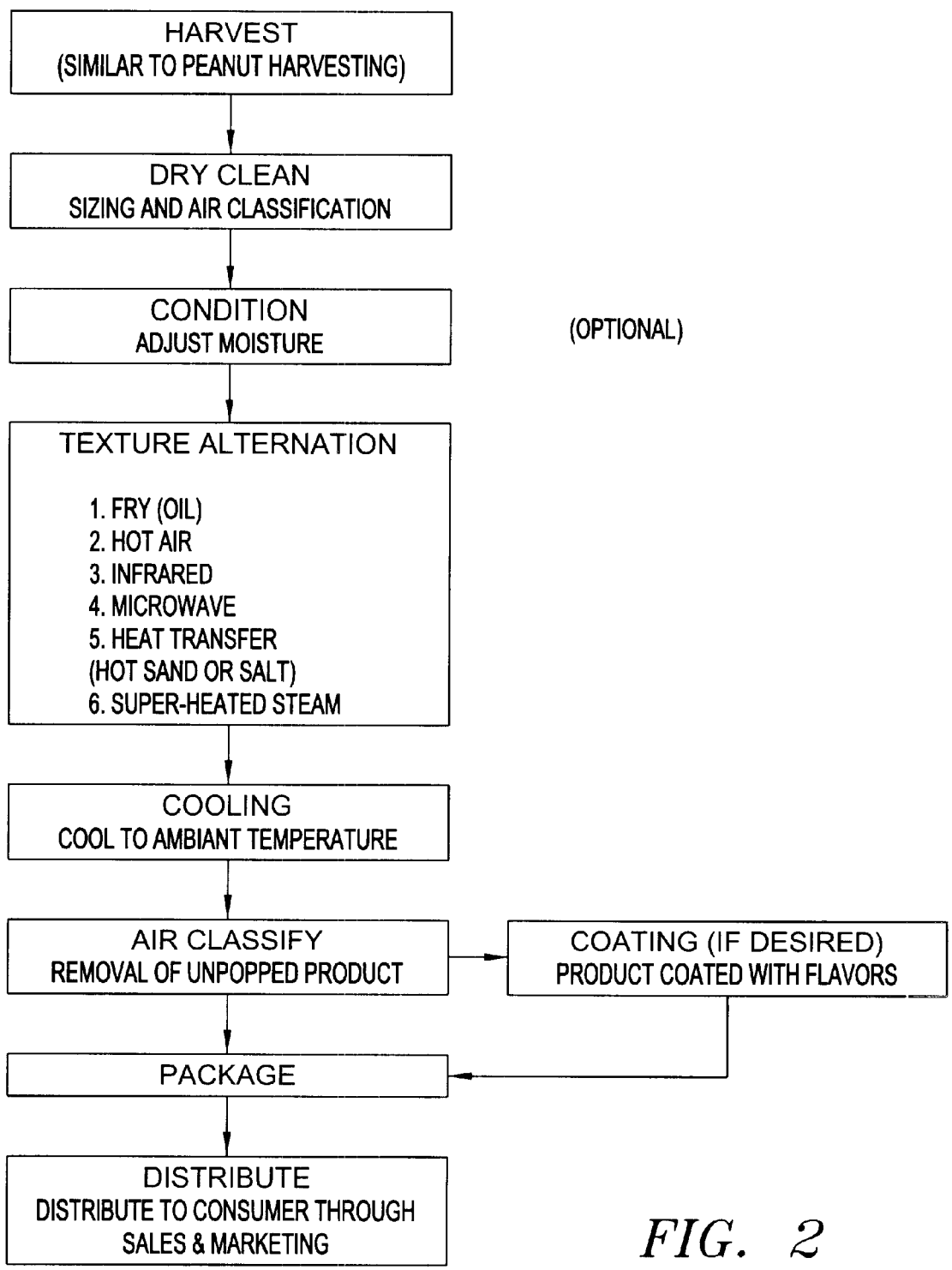
FIG. 2 is general processing scheme for beans according to the invention.
Figure 3:
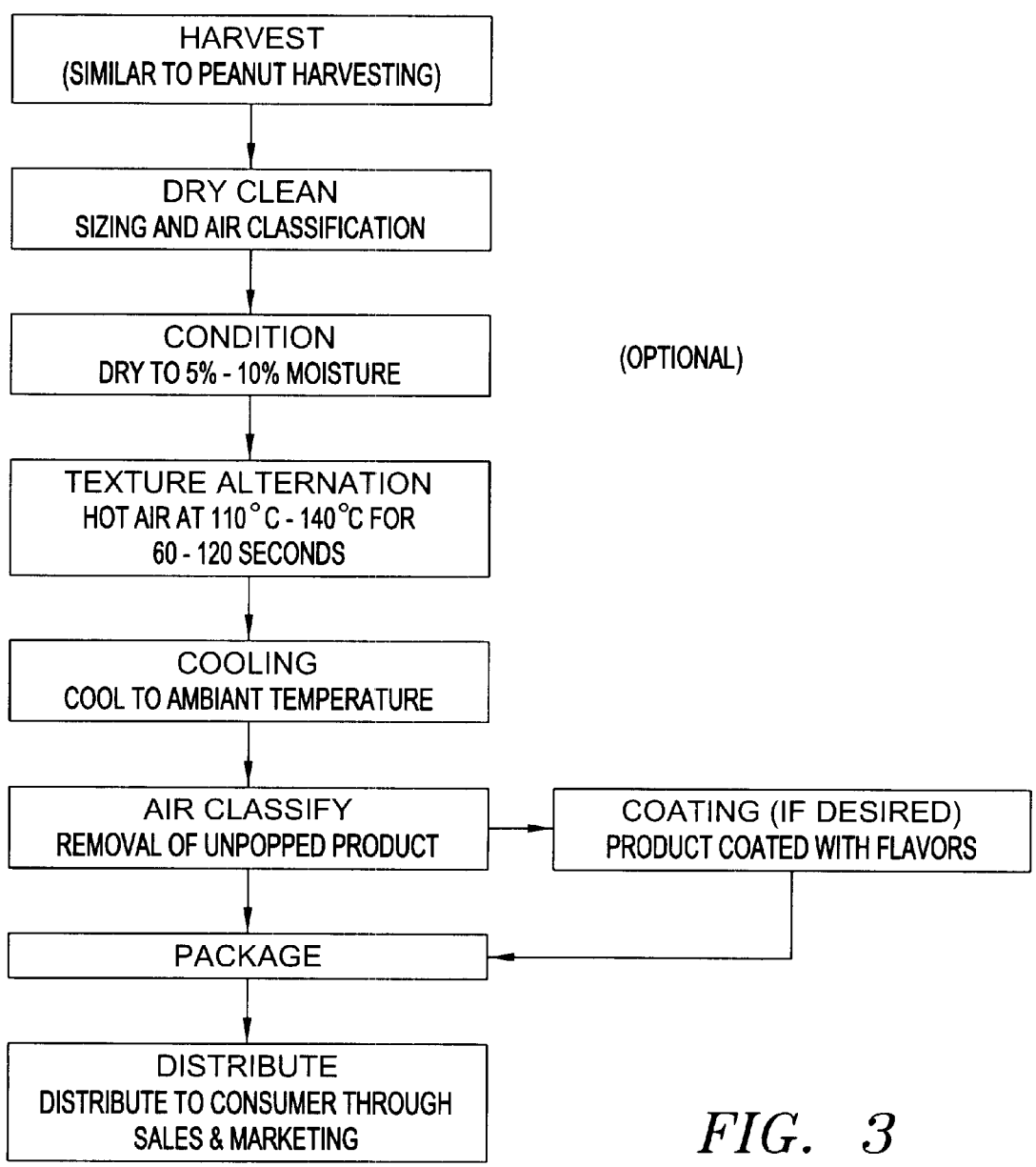
FIG. 3 is a more specific processing scheme for beans according to the invention.

The following scheme was used to combine the desired traits of early maturity, bush type growth habit, synchronous fruiting, photoperiod insensitivity, and the ability to produce beans that pop into genotypes well adapted to bean growing regions in the United States (see FIG. 1). Twelve different crosses between Nuñas and United States cultivars were made and a large number of individuals and lines were evaluated for the desired traits. The scheme described below is only one scheme which resulted in the development of two lines that exhibited the preferred traits. One of skill in the art will understand that the particular order, number and duration of the breeding steps may be varied and still produce a plant of the present invention.

Another scheme useful to produce the plants of the present invention is a single cross of a nuña accession and a *Phaseolus vulgaris* cultivar exhibiting the characteristics of early maturity, bush type growth habit, synchronous fruiting, and photoperiod insensitivity followed by selection of a large number of $F_2$ individuals for the desired traits.

Further, one of skill in the art will understand that equivalents to the particular plants used in the breeding process may be available and used to produce the plants of the present invention. Nuñas that are useful in the present invention are those that pop or expand upon heating. In addition to those already discussed these include, but are not limited to, accession numbers W6 4296, W6 4297, W6 4298, PI 298820, PI 298822, PI 298824, PI 316014, PI 316016, PI 316017, PI 316018, PI 316019, PI 316020, PI 316021, PI 316022, PI 316023, PI 316024, PI 316025, PI 316029, PI 316030, PI 316031, PI 390771, PI 390775, PI 511763, PI 511767, PI 531862, PI 577677, PI 577678, PI 577679, PI 577680, PI 577682, and W6 18720. *Phaseolus vulgaris* cultivars that are useful in the present invention include those that exhibit the characteristics of early maturity, bush type growth habit, synchronous fruiting, and photoperiod insensitivity. For example, such *Phaseolus vulgaris* cultivars include but are not limited to small white, small red, navy, dark red kidney, light red kidney, black or black turtle, pink, pinto, cranberry, and canario. Andean gene pool germplasm is preferred. One of ordinary skill in the art will understand that within the above listed market classes of *Phaseolus vulgaris* cultivars there are many varieties, such as pink: Sutter Pink and Telano; light red kidney: Linden and California Early Light Red; dark red kidney: California Dark Red Kidney and Montcalm; pinto: NW 590, Othello, RNK 101, UI 196, Flint, Fiesta, UI 126, UI 129, Olathe, UI 114; small white: Aurora; small red: Ruffus and Red Mexican; black: Black Turtle Soup 39, Midnight, Blackhawk, and Raven; navy: Huron, Avanti, Fleetside, Seafarer, Albion, and Midland; cranberry: Taylor. These varieties and the like are also useful in the present invention. Such varieties are readily ascertainable, for example from listings by the U.S. Department of Agriculture and from generally available commercial sources.

Cross California Early Light Red Kidney to PI316013 (Home Greenhouse), Spring 1992

Hybridization of the Peruvian nuña accession No. PI316013 with the early maturing red kidney variety 'California Early Light Red Kidney'. A kidney cultivar was chosen as one parent since both parents would then be members of the Andean genepool of common bean and therefore the progeny should have higher performance than inter-genepool crosses such as between Andean×Meso-American genepools. Also, the kidney cultivar would be a donor of the traits of early maturity, bush type growth habit, synchronous fruiting and photoperiod insensitivity.

Advance $F_1$ to obtain $F_2$ Seed (Home Greenhouse), Summer 1992

Plant $F_2$ to obtain $F_3$ (Home Greenhouse), Fall 1992

Approximately 200 $F_2$ plants were grown, selected for early maturity, bush type growth habit, synchronous fruiting and evaluated for popping at maturity.

Four methods, hot air, microwave, hot skillet and deep frying in oil, can be used to initially screen for the ability to pop. All methods were successfully used to pop the beans of the current invention. However, hot air and frying gave the highest percent popped beans and the most uniform product. Hot-air was chosen as the preferred screening method as this was the method envisioned to be most likely method adopted to commercially produce a low-fat popped bean product.

A modified hot-air popcorn popper (Presto) was used to screen beans from individual $F_2$ plants. Ten beans form each $F_2$ plant were placed in the pre-warmed popper for 1.5 minutes, after which the sample was visually inspected for frequency of popped beans and extent of expansion. Remnant seed of $F_2$ individuals with the highest percent of popped beans and greatest expansion were selected for further evaluation. A similar protocol was used to evaluate ability to pop in subsequent generations. Popping was carried out at a moisture level of about 9 to 10%. Applicants have discovered that the percentage of moisture is a significant factor in determining the ability of the beans to pop. Popping is substantially reduced above 12% moisture and below 5%. Moisture is measured on a dry weight basis by weighing a sample of beans at the time of popping having first dried it for at least 3 days at 105 C.

Plant Selected $F_3$(N15) Obtain $F_4$ (Home Greenhouse), Spring 1993

Approximately 20 $F_2$ plants were selected for early maturity, bush type growth habit, synchronous fruiting and identified as producing beans that exhibited popping. About 10 $F_3$ plants from each of the 20 single plant selections were grown. Ten single plant selections were made from 5 of the $F_3$ families. $F_3$ family No. 15 (N15) was an elite appearing family and several single-plant selections were made from it. Sent Ten Selected $F_1$ Families for Increase and Inbreeding to Hawaii (Hawaiian Research Ltd., Molakai), Summer 1993

The ten $F_4$ families (which included five N15 selections) were sent to Hawaii for increase and inbreeding. The N15 lines produced seed in less than 100 days. The seed from each family was bulked and sent back to California.

Grew Ten $F_5$ Bulks (La Sierra Greenhouse), Winter 1993

The ten bulk $F_5$ families were grown in the greenhouse during the Winter of 1993. Single plant selections (early maturity, bush type growth habit, and synchronous fruiting) were made from each family and evaluated for popping. The $F_6$ line N15-2-1-1 was among the selections made. This line possessed earliness, bush type growth and synchronous fruiting, but exhibited uneven popping characteristics and only moderate yield potential due in part to partial photoperiod sensitivity with respect to reproductive development. Under high temperature, long day conditions, bean lines with partial photoperiod sensitivity exhibited arrested floral bud development and few pods are set.

Cross $F_1$ of PI316032×CELRK with N15-2-1-1

California Early Light Red Kidney was hybridized with PI316032 (a peruvian nuña accession with excellent popping characteristics). This $F_1$ was then crossed with N15-2-1-1 in order to transfer additional genes or modifier genes for popping from PI316032 and more complete photoperiod insensitivity and local adaption from CELRK to N15-2-1-1. The use of this three-way cross allowed simultaneous improvement of popping and adaptation in a single cross.

Advance $F_1$ (Del Valle Date Gardens-Indio), Spring 1994

Ten plants of this three-way cross $F_1$ were advanced and approximately 1000 $F_2$ beans were obtained and bulked.

Plant $F_2$ (Rheingans Ranch-Temecula), Summer 1994

The $F_2$ population of this cross was grown under long photoperiod conditions. Plants were visually selected at maturity for the desired combination of adaptive/agronomic traits (early maturity, bush type growth habit, synchronous fruiting and photoperiod insensitivity), as well as for prolific podding. popping ability of 400 selections was again evaluated in a hot air corn popping machine. Because the inheritance (number of genes, dominance, and existence of epistasis and modifiers) of the popping trait was not known, a large number of single-plant selections were evaluated for their popping characteristics. About 40 individuals exhibiting the best popping characteristics were selected.

Plant Selected $F_3$ (Home Greenhouse), Fall 1994

The 40 $F_4$ families were planted in the greenhouse with 10 individuals per family. Another round of single-plant selection was conducted for early maturity, bush type growth habit, synchronous fruiting and the ability to pop. About 200 individuals were evaluated for popping using a hot air popper.

Plant Selected $F_4$ Families (U. C. Riverside Coachella Valley Agricultural Research Station), Spring 1995.

Thirty-five $F_4$ families were grown in single row plots 20 feet long. Single plant selection was conducted again for adaptation and agronomic characteristics (early maturity, bush type growth habit, and synchronous fruiting). Selection for the ability to pop was then conducted with a hot air corn popper on about one hundred selections. Twenty-one families were selected.

Plant the Selected Twenty-one $F_5$ Families (U. C. Riverside Field Station, Field 9A), Summer 1995

The 21 families were planted in single row plots, 20 feet long. Selection for agronomic characteristics (early maturity, bush type growth habit, synchronous fruiting and photoperiod insensitivity) and for the ability pop was conducted. Two $F_5$ families were selected for multiplication (Selection from Field 9A rows 849 and 855) and the seed bulked. These are 849-5 which have solid dark red, medium sized, (0.32 mg/seed) grain and 855-1 which have white with dark purple speckling, medium sized (0.35 mg/seed) grain. These families exhibit the desired traits of early maturity, bush type growth habit, synchronous fruiting, photoperiod insensitivity and produce popping beans.

Seed Increase $F_6$(Home Greenhouse), Fall, 1995 and Spring, 1996

Seed Increase of 849-5 and 855-1 (Tarke Plot, Tom Stine, Grower, Meridian, Calif.), Summer 1996

Seed Increase of 849-5 (Muleshoe, Tex.) Summer 1996

Seed Increase of 849-5 and 855-1 (Indio, Joe Manion Grower), Spring 1997

Nine acres of each variety were grown.

Definitions Applicable to Popping and to Snack Foods

By "snack food" is meant edible material—that is, material that is capable of being chewed and consumed as a matter of convenience. The term is subsumed into the broader term "foodstuffs", which connotes a more complex, highly processed food, or one that is used more as a staple food than as a fast, sporadic, snack food.

By "pop" or "popped" is meant the expansion or puffing of the grain and softening in texture. Prior to popping, the grain is so hard as to be virtually inedible, while the popped product is relatively soft with a "chalky" texture that resembles toasted edible soybean or peanuts. Popping may or may not connote an audible effect associated with the phenomenon and/or a flavor conversion. Popping is not the same as boiling, drying, baking, or soaking the grain. The resulting popped grain is distinguishable from grain which has not been treated by popping, based on properties such as density, moisture content, and texture. The moisture content of popped product is less than 30%, preferably less than 15%, and more preferably still less than 9%.

By "texture" is meant primarily hardness and compression force characteristics necessary to crush or deform a snack food. Such may also connote a granular as opposed to a homogeneous soft consistency in the food, and various forms in between. In terms of "popping," density is also lessened and therefore a function of texture. The texture of popped product is relatively soft with a "chalky" texture that resembles toasted edible soybean or peanuts, or that can be rendered so.

By "suitable heat energy" is meant one that contributes or effectuates popping as described above. Preferably, it also connotes a temporal and temperature sufficiency such that the kernels are substantially unburned and non-charred at the conclusion of popping. As known in the art, higher temperatures or higher energy wavelengths will require less time to cook/pop and vice-versa.

By "grain moisture content" or "seed moisture content" is meant roughly the amount of water inside the seed that can modulated, for example, by hydration or drying of the beans, or other manipulation. Such manipulations can also be coordinated with artificial flavoring steps.

By "peanut-substitute" is meant a snack food product with similar taste, texture and/or otherwise consistency of peanuts. This may or may not be a consequence of artificial flavoring additives or enhancements as known in the food arts.

By "processed" is meant converting from a raw form to a man-made one, such as in harvesting, which concentrates produce. The term can also connote conversion of a substantially inedible snack food to a substantially edible one, for example, by cooking or popping.

By "conditioning" is meant a hydration and/or dehydration/drying step(s) to achieve a suitable starting moisture content as defined herein that enables popping. In addition to rendering beans more susceptible of popping (or in some cases enabling popping altogether), the procedure may also be coupled with artificial flavor addition(s).

By "palatable" is meant edible, preferably desirable in taste.

By "particulate matter" is meant granular heat-sinking objects, such as sand or salt, that when heated and mixed with unpopped beans conveys heat energy to effect popping of said beans. Preferably such particulate matter is conveniently separable from the popped product.

II. Popping

A further aspect of the invention concerns the processing of raw and otherwise inedible beans into edible and healthy snack foods using rapid heating means such as hot air, oil, microwaves, infrared waves, superheated steam, or hot particulate matter such as sand or salt to effectively "pop" the beans. Some beans are more amenable to popping than others. Applicants have found that those cultivars that are not initially suitable can be converted to such using a conditioning step that establishes a suitable moisture content for popping. The Applicants have noted that moisture content correlates with popping ability. Thus, by manipulating moisture content, one can manipulate popping ability.

Hot Air Popping

Hot air popping is described, for example, in U.S. Pat. Nos. 4,152,974, and 5,421,253. This method of popping has been referred to as "dry" popping and utilizes a stream of hot air as the popping medium. It has a number of advantages over wet popping. For example, the additional calories and expense associated with oil popping are avoided. Moreover, various commercially available apparatuses use the stream of air to agitate the beans and prevent non-uniform heating and popping. Thus, the procedure is relatively efficient in terms of converted, popped product. Corn kernels can be cooked using hot air of about 110–250° C. (~230–500° F.). Beans can be popped using similar temperature parameters. The Applicants have had success using temperatures of about 110–240° C.

Hot Oil Popping

Hot oil popping is described, for example, in U.S. Pat. Nos. 5,694,830 and 5,409, 729. The oils and fats used should be edible, preferably from plant sources having polyunsaturated compositions that are considered healthier and lighter, for example, olive oil, corn oil, sesame seed oil, soybean oil, sunflower oil, peanut oil, etc. Soybean oil is considered to impart a preferable "buttery" flavor to popcorn and may impart a characteristic to popped beans. The temperature used to pop the substrate can vary depending on the type of oil used, but generally the range 150–205° C. is suitable, with temperatures in the range of about 180–190° C. considered optimal. The degree of individual seed pop (expansion size) generally varies proportionately with temperature; increasing temperature correlates with better expansion. Popcorn typically takes 2–5 minutes to pop. The Applicants have noticed that beans typically take less time. The preferred amount of oil to be used is about 1–30:1 oil:seed (w-w), with higher ratios being preferred. There is no apparent upper limit to the amount of oil that can be used but economics dictate using the specified range.

It should also be noted that less time is generally required for hot oil and hot air than for the methods that follow.

Infra-red Popping

Infra-red popping is described, for example, in U.S. Pat. 5,478,986. Infrared radiation is of a higher wavelength and hence lower energy level than microwaves. The wavelength borders visible and near visible wavelength spectra and filters are available to select for specific desired wavelengths emanating from a source. This method of popping has the advantage in that high intensity use of these longer wavelengths allow a lesser penetration that cooks predominantly just the husk of the seed, leaving the interior alone. This has the effect of focusing the cooking energy and accelerating the popping process. The technique may take as little as 15 seconds. Additionally, there is minimal burn on the popped product, as it is predominantly the inner, starchy layers that are exposed upon popping and these layers are white and reflect light, thereby minimizing continued cooking of the fleshy interior of the seed. This method is also relatively energy efficient in that the walls of typical hardware units reflect light and therefore economize administered energy.

A typical unit contains quartz-halogen tungsten lamps, or equivalent means such as quartz arc lamps. Typical quartz-halogen lamps of this type convert electrical to black body radiant energy having a range of wavelengths from 0.4 $\mu$m with a peak intensity at 0.965 $\mu$m. These lamps can generally provide from 1–2 kW of radiant energy with a significant portion of the energy in the visible light spectrum. It is easier to configure larger infrared devices having multiple lamps than it is microwave ovens. Therefore, from a bulk commercial standpoint, this method offers a distinct advantage. Typical ovens can use one to as many as ten or more lamps operated in unison.

Microwave Popping

Microwave popping is described, for example, in U.S. Pat. Nos. 5,743,174, 4,450,180, 4,548,826, 4,691,374, 5,044, 777, and 4,724,290. Microwaves are a form of electrical energy that is similar to radio and infrared waves. Domestic microwave units emit a frequency of about 2450 megahertz, which is the frequency reserved for industrial, scientific, and medical uses of the shorter radio waves. This corresponds to a wavelength of approximately 12 centimeters. Commercial supply of microwaves is abundant. Full size microwaves (larger than 1.2 cu. ft.) are available from 650–1,000 watts; intermediates: 600–800 watts; compacts: 500–700 watts. Most microwave instruction times on packages and in recipes are based on a 600-watt oven. A higher wattage unit heats more quickly; a lower wattage unit cooks more slowly. One of ordinary skill in the art can manipulate the time sufficient to pop Product accordingly.

Steam Popping

Steam popping or roasting is described, for example, in U.S. Pat. No. 5,681,607. The subject patent describes a process for roasting coffee beans that Applicants believe will also accommodate practice of the instant invention, with certain modifications understood to those of skill in the art. For example, popping borrowing this method will utilize a pressure and temperature controlled vesicle with a means for injecting superheated steam of between about 150 and 400° C, for about 50–300 seconds, at a pressure of between about 6.5–20.0 bars G. This is followed by a rapid pressure decrease and/or temperature drop that results in effective expansion (popping) of the beans so exposed. This can be accomplished, for example, by a rapid unsealing of the pressurized unit to equilibrate with atmospheric or subatmospheric pressure, and/or subjecting the vesicle's periphery to cooling water so as to effectively lessen the internal pressure. The United States Patents referenced in the section governing starch, below, are also helpful.

Applicants have found that suitable popping parameters according to the preceding are, or are likely, attained without appreciable experimentation even though the beans of the invention likely have a distinct constitution, appeal and set of cooking parameters.

There are primarily two components to the cooking process, exclusive of breeding that permit successful popping: selection or conditioning of beans to have a suitable grain moisture content for "popping," and application of a heating means at temperature and time sufficient to effect popping. These parameters, as discussed above, will vary depending, for example, on the precise beans used and the specific means of heating applied. Effective variance and optimization of these parameters, however, is well within the skilled artisan's knowledge and abilities.

As also described, popping is denoted by a texture alteration of the cooked grain that is manifest as an expansion (shape/volume transmutation), coupled with a concomitant softening and lessening of grain density. The process also typically results in the loss of moisture such that, initially and prior to processing, the beans have a defined moisture content or range of moisture content that is lessened on popping. This loss of moisture is usually manifest by the give-off of steam energy and hence water weight.

III. Conditioning

Those beans that are innately recalcitrant to popping or otherwise yield sub-optimum popping may be artificially, ie. chemically or physically treated to yield a suitable starting product that will pop. The easiest way to achieve suitable moisture is to simply dry (dehydrate) the seed to the appropriate moisture range. The Applicants have found it convenient to first hydrate and then dehydrate, for example, by immersing in water for a sufficient period of time, followed by slow drying to an appropriate moisture content. The hydration step may be facilitated by the use of a pressure-cooker or humidifier that allows for the accelerated upward adjustment of moisture. Commercial drying machines are available that permit controlled temperature and humidity drying. (Proctor & Schwartz Inc., Horsham, Pa., USA). Those of skill in the art are aware of equivalents. The drying should be slow as not to fracture the bean prematurely; premature fracturing eliminates or minimizes the potential for desired popping.

Beans according to the invention may be "blanched" (optional) as known in the art as part of a conditioning step, or separately to remove the skins for their own utility as a food snack while retaining and separating the popped beans. Blanching as used herein is synonymous with soaking and heating the beans simultaneously to hydrate them, but also as a means of removing their skins. Traditionally, such procedure was used to strip the beans of "skin" that made the beans more difficult to cook, and less appealing as a finished product. The Applicants have discovered that blanching does not necessarily result in loss of the claimed beans' skins, and that the skins are not necessary for popping. Moreover, the Applicants have discovered that popping results in the skins dissociating from the popped beans anyway, and that the skins are readily separable from the beans according to the classification schemes noted earlier. The applicants have discovered that these "bean skins" have a separate appeal and use in the food industry as a potential snack food. Therefore, in preferred embodiments, the skins are left on and separated at the end of the popping process for maximum yield and efficiency.

To the extent that non-popping dispositions are attributable to particularly hard beans, these can be weakened by chemical and/or mechanical treatment, e.g., blanching. Such treatment should preferably not involve caustic chemicals that are harmful when ingested. A cleansing or washing step should therefore be incorporated to insure chemical clearance. preferably, conforming cultivars are selected to begin with, or else conditioned without the use of caustic or toxic chemicals. However, it is possible that some nonconforming cultivars possess other unique and desirable characteristics, for example, yield, ease of growth, superior nutrition, etc. for which such processes may then be used to render conformity. plant breeding is another possibility for overcoming obstacles to popping.

By selecting and propagating desirable traits, one can produce new plants bearing new traits and combinations of traits. Although the application is enabled for the breeding and consolidation of various defined traits having commercial appeal, and in which popping is promoted, this is by no means a representation that other traits cannot also be involved, and optimized using similar methodologies to result in an even more appealing product. One of skill in the art, using the routine selection and breeding instructions described herein can accomplish this.

As discussed above, the Applicants have determined that moisture content has a strong correlation with popping success. For example, at moisture contents of about 15% or more, no or minimal popping is observed. The beans fail to expand.

Instead, they take on a darkened, hard exterior. At moisture contents of about 12% or less, popping occurs. The Applicants hypothesized that expansion (popping) of a seed having preferable moisture contents, as discussed, might be the product of rapid vaporization pressures within the seed that quickly overcome the seed shell structural fortification. Higher moisture contents likely take longer to heat, thereby resulting in an equilibration across the seed coat instead of a rupturing steam energy differential. Applicants believe they have confirmed this, but nevertheless do not wish to represent this theory as necessarily correct or limiting.

Applicants as well as others have also noted and implicated starch properties in popping success. See, e.g., U.S. Pat. Nos. 3,652,294, 3,800,050, 4,990,348, 4,409,250 and 5,320,858. For example, the author has noted that parboiling rice to effectively pre-gelatinize the starch within, coupled with a subsequent cooling step under controlled pressure and humidity, results in a later effective "popping" of the rice on rapid heating. Starch is a common product in flour, and a significant component of grain endosperm. While beans are not a monocot grain, they nevertheless possesses starch that can and may be gelatinized in the conditioning and/or popping process. Consistent with popping ability, those cultivars that pop without conditioning have a starch content of ~50–65% and a moisture content as previously noted.

Optimum and preferred aspects and embodiments include products generated from, and processes entailing, the popping of raw or preconditioned beans having a suitable grain moisture content, preferably between about 5–15%, more preferably about 7–12%, and most preferably about 7–9%. When exposed to temperatures of between about 110–260° C, preferably about 170–240° C, for approximately 0.5–10 minutes, more preferably about 0.5–5 minutes, and most preferably about 50 seconds to about 1.5 minutes (depending on the exact method used), yields the desired product. Other temperature ranges and time spans may be determined to be appropriate depending on the specific heating technique employed, the exact starting product, and other environmental conditions. The Applicants have delineated particulars in the examples below that worked best for Applicants as of this filing. The Applicants, however, does not wish these particulars to be limiting, especially in recognition that more suitable parameters may ultimately be identified. The Applicants consider the broad temperature ranges listed herein, apart from the examples, to likely suffice, all factors considered. The goal is to effect popping, preferably without burning or charring the beans.

III. Additional Processing

Once popped, the beans may be artificially or naturally cooled as part of an integrated, commercial processing procedure. Preferably the procedure does not allow the resulting popped product to accumulate moisture. Optionally, the popped product is culled of unpopped beans by, for example, an air classifying scheme that is common within the food-processing industry and known to those of skill in the art. (See, e.g., popcorn instrumentation available commercially from C. Cretors and Co. (Chicago, Ill.)).

Integrated into the process may also be a flavoring step wherein the popped beans are coated with any one or a combination of commercially available flavorings, preferably non-allergenic, artificial nut flavorings such as peanut, cashew, hazelnut or walnut. Mixtures bearing different flavors are also contemplated. The flavorings need not be nut and may, alternatively or in combination, be selected from generic or specialized sweeteners, salts, butter or other butter substitutes, spices, and other flavor embellishers such as caramel or cheese.

Flavoring may occur before, after, or during popping, for example, according to the procedures as described in U.S. Pat. Nos. 5,688,543, 5,443,858, and 5,750,166, and 5,753,287. Other procedures are also possible and within the skill of one skilled in the art. Those in the food industry, for example, will see a great range of potential for flavoring of popped and unpopped product. Preferably, but not essentially, the flavoring additions will minimize introduced calories, thereby preserving the innate healthy nature of the Product beans relative to peanuts, cashews, and other processed foods. The Applicants have also observed that water-based flavorings may be added to whole, popped beans without compromising structure and texture of popped product. This contrasts, e.g., with popcorn, which tends to compress upon addition of aqueous flavoring.

Preferred embodiments include popped beans that are optionally flavored and packaged as a snack food or crouton-like salad supplement. Other product formulations and configurations, i.e., candy or health bars with popped beans as an ingredient are also contemplated. Mixtures with, e.g., raw or dried fruits, fruit juices, beans, and nuts are contemplated. Various product configurations may be held together by, for example, honey, caramel or molasses and contain, for example, raw sugar, raisins, dates and/or figs. Chocolate may be added in less health-conscious embodiments.

Once the beans have been configured as desired, a terminal step in the food manufacturing process is packaging—something well known in the art. This packaging may occur before or after popping. For the former, unpopped beans are supplied in microwaveable bags like exist for popcorn, and that are commercialized with directions for cooking. U.S. Pat. Nos. 5,770,839, 5,488,220, and 5,681,607 describe such bags in detail. Alternatively, the unpopped beans may be supplied in jars or other containers from which a set number of beans can be dispensed and cooked/popped according to directions supplied therewith and corresponding to methods included herein.

A particularly attractive embodiment of the processed bean is as a blended, homogenized spread that has a consistency and/or taste like peanut butter. To this end, the Applicants have applied for a federally registered trademark for the name Beanut Butter™. The mark Bean Nuts® has already been acquired for processed beans, generally.

A homogenized buttery blend may be achieved using methods well known in the food arts, e.g., by creating a paste out of the popped beans using, e.g., a commercial grinding apparatus such as a comminuter, colloid mill, hammermill, attrition mill, or other disintegrating device. This paste may have to be supplemented with other oils if the innate oil within the popped beans is insufficient, or to otherwise vary consistency of the finished product. Additives such as stabilizing agents, emulsifying agents, salt, and/or sweetening agents may be further included, and is well known in the food arts. This is discussed in the peanut context, for example, in U.S. Pat. No. 5,240,734 issued to Izzo et al., U.S. Pat. No. 5,436,023 issued to Avera, U.S. Pat. No. 5,366,754 issued to Rudan et al., U.S. Pat. No. 5,714,193 issued to Fix et al., 5,948,954 issued to Horn et al., and U.S. Pat. No. 5,518,755 issued to Wong et al. Those patents and all others cited in this patent application are hereby incorporated by reference.

Various examples to follow highlight and illustrate the essential underlying conditioning and popping processes, and the unique resulting products and product configurations that are within the spirit of the invention. Those of skill in the art will know how to pursue the various aforementioned embodiments. Those embodiments, as well as the examples that follow, are intended merely to illustrate the possibilities and are not intended to limit the true scope and spirit of the invention.

EXAMPLES

Example 1

Popping Using Hot Air

Beans are pooled into a hot air popcorn-type popper, e.g., Presto® (small-scale) or Cretor's® (large, industrial scale) and cooked roughly following the manufacturer's guidelines for popcorn. This corresponded to approximately 1–2 minutes of exposure time at about 170–240° C.

The "skins" of the bean separate naturally from the popped bean upon popping and are readily separable according to common air classification schemes noted earlier. The skins and the beans may then be separately packaged, or packaged together as food snacks. Additional flavorants and processing steps may also be employed. This general use of the skins to maximize utility and return on starting product also applies to the examples noted below.

Example 2

Popping Using a Microwave Oven

This was performed substantially as in example 1, except that the beans were positioned on a glass plate within a 1000 W microwave oven and cooked on a regular setting for 2–4 minutes, periodically gauging the extent of pop. This can vary for various standard home units, as described above.

Example 3

Popping Using Hot Oil

Beans were overlayed over a thin layer of cooking oil in an encapsulated vessel and a heating element source was supplied to heat the oil to between about 165–170° C. (~330–340° F.) to pop the beans contained within the vessel. The vessel served to contain volume and pressure so that the heating was performed rapidly and efficiently. The Applicants have observed that seed moisture content may be elevated approximately 1–2% and still be successful using this method relative to those methods employing hot air, etc. Also, flying in oil was observed to take less time than the other methods, ~30 seconds–1 minute.

Example 4

Popping Using Particulate Matter

Beans are mixed with finely particulate and preheated (~150–200° C.) sand or salt in a vessel for approximately 30–60 seconds to effect popping. Unpopped beans were then separated from popped beans by a sieving scheme. The exact time of cooking depends on the identity and coarseness of the particulate matter used, as well as temperature, etc. During this type, or any type of heating method, agitation can be useful to stimulate uniform heating and to prevent burning of the popped product.

Example 5

Conditioning

Applicants have determined that, whereas a simple drying step may be sufficient to render a suitable moisture content for popping, a conditioning method that employs a hydration step works in the event that mere drying is insufficient. For example, a poor-popping cultivar may be positioned into an open kettle having water at atmospheric condition and boiled for approximately 90 minutes such that the seed moisture content becomes approximately 50–60%, or else the seed was placed in a pressure steam cooker for approximately 45 minutes. Lesser hydration may suffice. The resultant seed was then slowly dried at approximately 80° C. and 20% relative humidity until the seed moisture content was suitable for popping (less than 15%, and depending on the popping method used and other factors; 7–12% is generally effective for all methods). The seed was then popped according to any of the above methods, and popping efficiency found to be ~50% effective, whereas unconditioned seed of the same cultivar popped significantly less. Further optimization and variation to suit a given situation is within the skilled artisan's routine understanding and abilities. Multiple rounds of conditioning, as described herein, may be useful in some applications. The Applicants verified that the general conditioning step described above also works for other cultivars. The exact parameters used above can likely be modified with similar success.

Example 6

Beanut Butter™

This prophetic example borrows from Examples 1 and 2 of U.S. Pat. No. 5,714,193 issued to Fix et al., and significant variations on the core concept are envisioned. The components are essentially the same as described in those examples except for a substitution of popped beans for peanuts in an amount ranging from about 60–83.9% weight of the total ingredients. Sugar comprises about 5.8%, oil content varies between about 6.45%–12% (to compensate for bean weight), salt represents about 1.2%, molasses about 0.5%, stabilizer (e.g., hardened rapeseed oil blended with hydrogenated soybean oil) about 1.85% and emulsifier (e.g., mono and diglycerides of palmitic and stearic acids) about 0.3%. The popped beans are ground to a paste in a milling device and transferred to a mixing tank, to which is then added the other ingredients. The tank is held at a constant temperature of about 150 degrees F. (~65.6 C.), and the items are mixed therein for approximately 30 minutes, after which they may be further processed according to well known art methods.

Other embodiments are within the claims.

What is claimed is:

1. A snack food consisting essentially of the skins of beans that have been popped, said beans of the plant species *phaseolus vulgaris*.

2. A snack food comprising popped beans of a *phaseolus vulgaris* bean plant, said plant exhibiting the phenotypic characteristics of early maturity, bush type growth habit, synchronous fruiting, and photoperiod insensitivity.

3. The snack food of claim 2 wherein said beans have skins and wherein said snack food consists essentially of said skins.

4. The snack food of claim 2 wherein said beans are substantially devoid of bean skins.

5. The snack food of claim 2 wherein said popped beans are popped at a moisture content of between about 5 and 12%.

6. The snack food of claim 2 wherein said *phaseolus vulgaris* bean plant is a hybrid bean plant.

7. The snack food of any one of claims 2, 4, 5, or 6 formulated as a blended spread.

* * * * *